United States Patent [19]
White et al.

[11] Patent Number: 5,632,894
[45] Date of Patent: May 27, 1997

[54] ARTERIAL BLOOD FILTER WITH UPWARDLY INCLINING DELIVERY INLET CONDUIT

[75] Inventors: George W. White, Lake Forest; Kenneth Galt, Seal Beach; Tichakorn Chaikumnerd, Huntington Beach; Jack W. Brown, Santa Ana, all of Calif.

[73] Assignee: Gish Biomedical, Inc., Irvine, Calif.

[21] Appl. No.: 265,243

[22] Filed: Jun. 24, 1994

[51] Int. Cl.⁶ .......................... B01D 19/00; B01D 35/30
[52] U.S. Cl. .......................... 210/436; 210/304; 210/456; 210/472
[58] Field of Search .......................... 210/420, 435, 210/436, 446, 453, 455, 472, 497.01, 497.1, 512.1, 188, 304, 456; 422/44, 45, 101; 55/458, 459.2, 461

[56] References Cited

U.S. PATENT DOCUMENTS

| | | | |
|---|---|---|---|
| Re. 32,711 | 7/1988 | Dickens et al. | 210/304 |
| D. 299,269 | 1/1989 | Pierson et al. | D24/21 |
| 4,411,783 | 10/1983 | Dickens et al. | 210/304 |
| 4,806,135 | 2/1989 | Siposs | 210/512.1 |
| 4,919,802 | 4/1990 | Katsura | 210/188 |
| 4,932,987 | 6/1990 | Molina | 210/304 |
| 5,039,430 | 8/1991 | Corey, Jr. | 210/436 |
| 5,203,999 | 4/1993 | Hughes | 210/512.1 |
| 5,312,479 | 5/1994 | Weinstein et al. | 210/188 |

*Primary Examiner*—John Kim
*Attorney, Agent, or Firm*—George F. Bethel; Patience K. Bethel

[57] ABSTRACT

A blood filter for use in filtering blood having side walls, a top, and a bottom joined to the side walls defining an axis with a filtration element surrounding at least a portion of the axis is disclosed. A delivery conduit delivers blood to the interior of the filter at an angle extending upwardly away from a plane which is perpendicular to the axis of the filter to form a vortex which is offset from the filter axis for release of entrapped air through an overlying top vent offset from the central axis, and an exit conduit connected to the interior of the filter element allows blood to flow from the filter element to an exit opening.

14 Claims, 4 Drawing Sheets

ARTERIAL BLOOD FILTER WITH UPWARDLY INCLINING DELIVERY INLET CONDUIT

BACKGROUND OF THE INVENTION

1. The Field of the Invention

The field of this invention lies within the blood filter art as it pertains to blood filtration during surgery. It more specifically relates to those blood filters that remove foreign matter and bubbles from blood passing in an extracorporeal blood circuit. The extracorporeal blood circuit often includes an artificial heart-lung machine or oxygenator. It can also include an artificial kidney as well as devices for separating blood cells and plasma components.

2. Prior Art and Improvements Over the Art

Many blood filters are known in the art. One particular related blood filter is that described in U.S. Pat. No. 4,919,802 which issued Apr. 24, 1990, entitled BLOOD FILTER, naming Yoshiro Katsura the inventor.

A second related patent is U.S. Pat. No. RE 32,711, reissued Jul. 12, 1988 and its original patent U.S. Pat. No. 4,411,783 respectively entitled ARTERIAL BLOOD FILTER WITH IMPROVED GAS VENTING naming Duane D. Dickens, and Francis M. Servas as inventors.

The U.S. Pat. No. 4,919,802 (802 Patent) specifically is directed toward a blood filter having a gas or air bubble separating section. The bubble separating section includes a conical top overlying a cylindrical chamber. The conical top allows gas or air bubbles to separate from the blood for discharge through a centrally placed air discharging vent. It relies upon a swirling flow or vortex within the filter chamber or container and conical top to create a de-bubbling effect.

The 802 Patent is specifically directed toward an inlet conduit that extends horizontally for introducing blood into the filter chamber. Further to the extent of delivery, the axis of the inlet conduit extends substantially parallel to a tangent line of the generally cylindrical filter chamber at the connection between the chamber and the inlet conduit, but is spaced a certain distance from the tangent line in a plane perpendicular to the axis of the cylindrical chamber.

In effectuating delivery of the blood into the chamber, the inlet conduit extends on a horizontal plane in a horizontal curved path of consistently decreasing radius, R1, toward the radius, R2, of the inner chamber from approximately its inlet to anywhere from 135° to 225° along the circumference of the chamber from its initial introduction point.

The U.S. Reissue Pat. No. 32,711 (711 Patent) also relies upon a substantially horizontal delivery conduit in a tangential direction which is not displaced as in the 802 patent. The horizontal input stream of blood is directed away from the central air vent. The patent teaches that this condition avoids interference with the venting. Further to this extent, it is seen that the horizontal delivery conduit delivers blood in the same manner as the 802 Patent around the interior wall portion of the blood filter chamber to create a vortex.

The 711 Patent further relies upon a sloped inner portion or filter cap element. The upper surface of the filter cap is symmetrical as to the longitudinal axis of the entire housing or chamber. The filter cap, furthermore, has its highest point at the center. A critical feature of the filter cap element is to exclude any localized points or regions of minimum height such as dimples, grooves, valleys and the like. Overlying the center on top of the filter cap is a dome shaped cover or lid which has a vent centrally oriented with respect to the axis of the entire filter chamber or body and the axis of the filter.

The teaching of both the 802 and the 711 Patents are directed toward a horizontal inflow which supposedly maintains laminar flow. This supposedly avoids the problem associated with the flow of the inlet blood impinging against the blood that is already in a swirling condition causing a disturbance in the blood inflow. In effect, the thought is to prevent turbulence so that blood and entrained air bubbles can readily separate.

In effect, the foregoing teachings of the substantially horizontally delivered blood flow, the tangential delivery as in the 711 patent and the tangential delivery as in the 802 patent which is parallel to and displaced from a tangent line of the chamber lying in a horizontal plane perpendicular to the axis of the chamber, as well as the symmetrical central filter cap of the 711 patent and the 802 patent, and the overall concept of bilateral symmetry with respect to the centrally placed air vent in the cap or the lid of the filter chamber have fundamentally taught away from the invention as established herein.

In particular, the aspects of the horizontal delivery of blood have been particularly noted. The Applicants herein have found that in preference to the horizontal delivery of blood, that an upward angular delivery of blood in the direction of the lid or top cover of the blood filter chamber is not only efficacious but improves performance substantially.

The upward momentum of the blood causes it to swirl around the top of the cover one or more times before it starts to flow downwardly. This swirling blood flow movement allows for entrained air bubbles to be removed in a more natural manner. The entrained air bubbles are placed in a natural state of buoyancy upwardly toward the offset vent of the filter of this invention. In allowing the directional component of the blood to achieve an upward vectorial velocity, the entrained air is also removed through its natural buoyancy being enhanced as to its direction of movement.

The upwardly directed blood inlet of this invention is deemed to be a significant step over the prior art in allowing the disassociation of air from blood to be filtered.

A second feature of the invention with respect to the prior art is an offset air vent. The offset air vent allows the placement thereof to be in the direction overlying the vortex. The upward velocity component of the delivered blood forms a vortex which is shifted or offset from the axial center of the blood filter chamber and lid. By placing the air vent overlying the general area of the shifted vortex, the entire function of disassociation and removal of entrained air through the offset vent is enhanced. This results in a non-conical filter chamber cover or lid.

Another feature of this invention is the conduit axis of delivery is angularly offset upwardly from a tangent line to the radius of the cylindrical filter chamber. By angularly offsetting the delivery of the blood upwardly into the filter chamber at the initial stages along and within a gently rising spiral channel, it is believed that less hemolysis is encountered due to the gentle nature of the introduction of the blood.

Another feature of this invention is that the axis of the introductory conduit at the point of introduction between the filter chamber and the inlet conduit is perpendicular to a line lying in a plane which is not perpendicular to the central axis of the filter chamber. It is believed that this feature enhances the release of entrained air from the blood when combined with the other features of the invention.

Another feature of this invention is the aspect of the air vent in the filter chamber cover being offset from the the axial center of the filter cap and filter, and filter chamber. This enhances the overall placement of the vortex while at the same time creating a non-tangential delivery of the blood in its flowing relationship.

A further feature of this invention relies upon the nature of the filter cap having the bottom edge chamfered and located below the inlet conduit to prevent entrained air bubbles from being retained under the filter cap.

A further feature of this invention that cuts down on hemolysis is the smooth and rounded delivery conduit. This allows the flow of blood to flow in a rounded smooth channel conforming to the configuration of the inlet conduit. This smooths the nature of the delivery of the blood so that it is not abruptly changed in direction, or introductory conduit configuration. The net result is lower turns and dramatic changes in blood flow which it is believed helps to lower the overall hemolysis of the blood to prevent undo damage to the cells thereof.

Another feature of the invention over the prior art is that the invention allows for a bypass of the filter through an integral bypass channel. This allows for the flow of blood to take place through the entire extracorporeal circuit by merely shifting introduction from the inlet of the arterial filter to the bypass circuit. This creates a continuity of flow with fewer components and a simpler circuit design over a standard bypass circuit.

In essence, this invention is believed to be a step over the prior art by providing upwardly angular introduction of blood into a filter for improved disassociation of entrained air. It further enhances the function by shifting the vortex in the direction of an offset air vent while at the same time allowing for improved flow features and non-entrapment of air in certain portions. The aspects of providing for an integral bypass also enables this invention to be a step over the art in allowing for ease and facility of use during its inclusion in the extracorporeal blood circuit of a user. And, due to its compact size, reduces the volume of fluid required in the extracorporeal circuit.

SUMMARY OF THE INVENTION

In summation, this invention provides for greater filtration capacity and removal of entrained bubbles of air for arterial filtration purposes in an extracorporeal filter circuit while at the same time reduces the fluid volume improving the facility of its use through an integrated bypass.

More particularly, the invention features an upward angular introduction of blood forming an upwardly delivered velocity component. The blood is introduced against the interior wall of a cover or lid to allow it to swirl around the cover for removal of entrained air bubbles.

The invention further features an offset air vent which overlies the centrally offset flowing blood vortex which more effectively allows for removal of entrained air bubbles. This is due to the fact that the velocity component shifts the vortex off center.

The angular or non-tangential introduction of the blood further enhances removal of air bubbles and results in less hemolysis to the blood. To this extent, a well configured and conformed flow path is provided in the same configuration of the rounded circularly cross-sectional introductory conduit. This serves to enhance the feature of maintaining low hemolysis and low cellular blood damage.

The arterial blood filter of the invention has an interior filter having a filter cap in which the axial center does not directly underlie the centrally offset air vent. A chamfered edge on the filter cap prevents entrapment of air bubbles.

Finally, the feature of a bypass built into the base of the filter chamber which allows for the filter to remain in the extracorporeal network without the filter function being retained therein is an improvement over the art. This facilitates the setup and overall facile usage of the filter of this invention.

As will be seen from the following specification and claims, this invention is a significant step over the art as summarily stated herein and which shall be expanded upon hereinafter.

DESCRIPTION OF THE PREFERRED EMBODIMENTS

General Configuration and Structure

Figure 1:
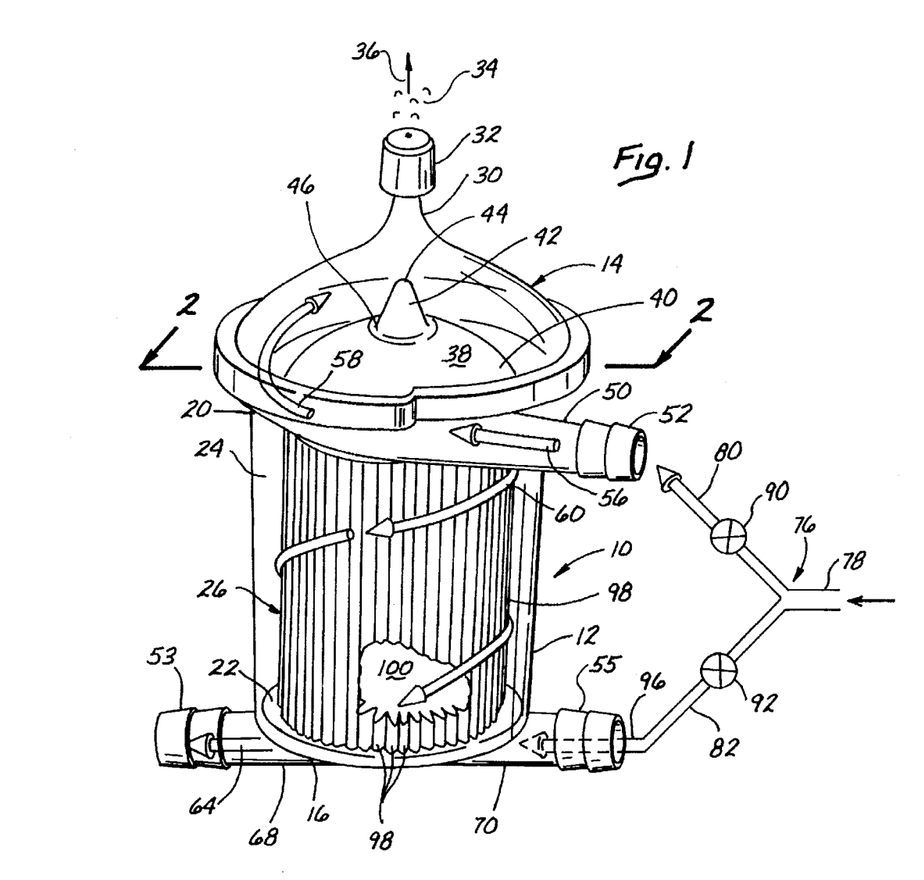
FIG. 1 shows a perspective view of the filter of this invention being shown in a clear plastic in order to observe the features thereof and includes a fragmented removal of the filter to illustrate blood flow.
Figure 5:
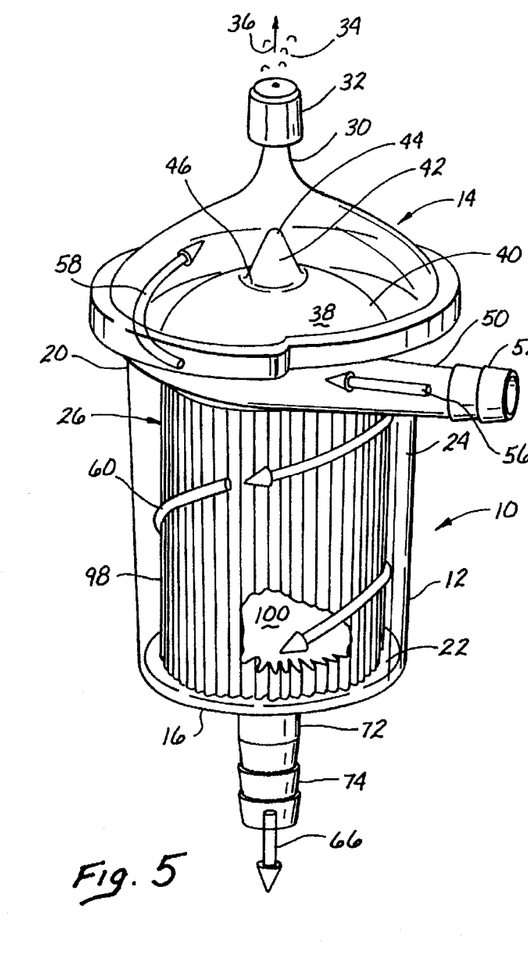
FIG. 5 shows the filter as shown in FIG. 1 without a bypass.

FIGS. 1 and 5 show a perspective view of the blood filter of this invention. The showings are of a graphic nature to illustrate the introduction and spiral path of blood flow with the arrow diagrammatic representation. FIG. 1 specifically shows a blood filter with a bypass option. FIG. 5 shows a blood filter without the bypass option.

Both FIGS. 1 and 5 have a representation of the blood filter in its preferred form respectively with and without the bypass. In particular, the blood filter 10 comprises a cylindrical side wall 12. The cylindrical side wall 12 is joined to a top cap or lid portion 14. The top cap or lid portion 14 is of a rounded asymmetric non-conical configuration.

The blood filter 10 has a bottom or base wall 16 which joins the rounded cylindrical side wall 12. The bottom or base wall 16 is joined in any suitable manner to the rounded cylindrical side wall 12.

The rounded cylindrical side wall 12, slopes inwardly toward the bottom or base wall 16. This provides an inwardly sloping space 24 that narrows as it approaches the bottom or base area 22. The rounded cylindrical side wall 12 terminates in a base wall 16 that is narrower at the bottom than at the top 20.

The space 24 surrounds a cylindrical pleated filter element 26 having a uniform wall diameter. As the rounded cylindrical side walls 12 of the filter 10 narrow toward the base wall 16, the space 24 between the rounded cylindrical side walls 12 and the cylindrical pleated filter 26 with the uniform wall diameter narrows until it reaches the base area or space 22 at the bottom or base wall 16.

The top cap or lid 14 of the filter 10 has a rounded asymmetric non-conical configuration that terminates at an outlet or vent 30. The outlet or vent 30 can be provided with a luer lock fitting 32 or any other suitable means for allowing air to escape therethrough. The escape of air from vent 30 is graphically shown in the form of air bubbles 34 that are moving in the direction of arrow 36. During operation, a tubular member is attached to the outlet or vent 30 which in turn is controlled by a stopcock.

Figure 6:
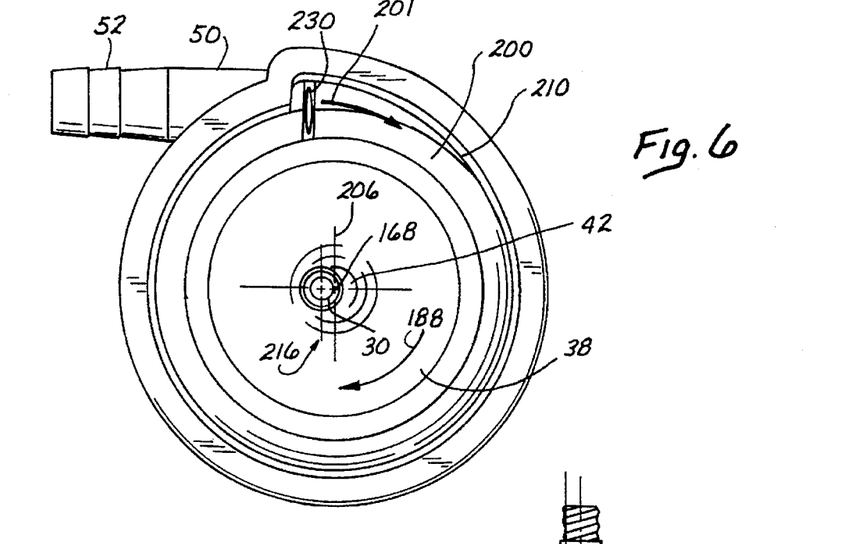
FIG. 6 shows a top plan view looking downwardly at the various elements of the filter to illustrate the offset vent, and non-tangential introduction of the blood.

The outlet or vent 30 as detailed in FIG. 6 is off center or offset from the central axis 168 of the filter 10. This offset orientation allows for improved disassociation of the air bubbles 34 that have been entrained from the blood that is flowing therein.

Figure 2:
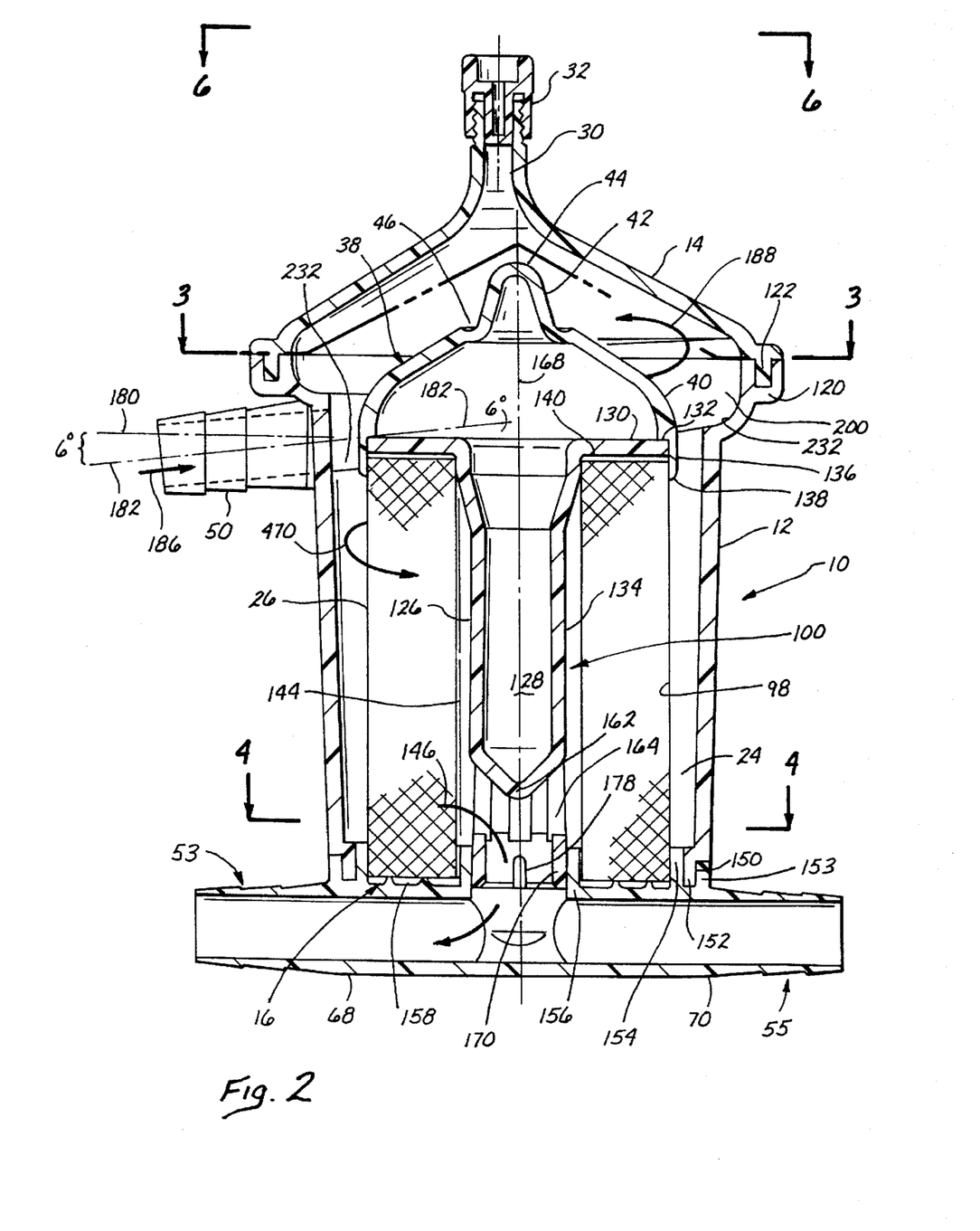
FIG. 2 shows a midline cross-sectional view of the filter along lines 2—2 of FIG. 1.

As shown more particularly in FIG. 2, the cylindrical pleated filter element 26 is provided with a dome or filter cap 38. The dome or filter cap 38 has a smooth rounded dome-like surface 40 which extends downwardly over the filter element 26 in the manner of a skirt and terminates upwardly in an upright rounded cone, teat or peak 42. The upright rounded cone or peak 42 has a round top 44. Between the dome or rounded surface 40 and the peak or rounded cone 42 is a circular groove 46 interfacing the dome and the rounded cone or peak. This provides a groove 46 that is lower than the dome or rounded surface 40 of the dome or filter cap 38.

The blood that is to be filtered by the blood filter 10 is delivered through an introductory passage or conduit 50. The introductory passage or conduit 50 is connected to a tubular portion of the extracorporeal blood circuit by means of a tubular connection or fitting 52. The fitting 52 comprises two sloped sections having angular edge portions that receive an expandable plastic tube thereover.

The flow of blood through the passage or conduit 50 is graphically shown being delivered in the form of arrow 56. Blood flows in the direction of arrow 56 in a manner to be described hereinafter. The blood is projected upwardly in the direction of arrow 58 since the blood flows in at an upward angle. This causes the blood to move spirally around the inside of the top or lid 14. This enhances the release of entrained air in the blood.

The blood then continues to flow in a downward spiral against the cylindrical filter pleats 98 in the direction of arrow 60 toward the bottom or base wall 16. As it descends in the direction of arrow 60 toward the bottom or base wall 16 it flows through the filter element 26. In the embodiment of FIG. 1 having the bypass unit, the blood from the filter element 26 exits in the direction of arrow 64. In the filter without the bypass as shown in FIG. 5, the blood exits in the direction of arrow 66.

The unit with the bypass shown in FIG. 1 comprises an outlet that extends into a bypass formed by an outlet portion or exit conduit 68 of the bypass and a bypass inlet portion or inlet conduit 70. The two portions 68 and 70 are both connected to tubular connections or fittings 53 and 55 respectively in the same manner as the tubular connection or fitting 52, all having sloped splines that engage an expandable plastic tube.

Outlet or exit conduit 72 of the filter 10 shown in FIG. 5 is a direct outlet. It is connected to a tubular connection or fitting 74 which also incorporates the splines, including two sloping circular portions which engage an expandable plastic tubular member to allow the flow of blood from the filter.

Looking more particularly at FIG. 1, it can be seen that the bypass inlet portion or conduit 70 has been schematically connected to a Y member connection or fitting 76. The Y member 76 has an inlet 78 from the extracorporeal blood circuit (not shown) with two branches or conduits 80 and 82. The branch or conduit 80 is connected to the introductory inlet passage or conduit 50. The branch or conduit 82 is connected to the bypass inlet portion or conduit 70. The branch or conduit 80 allows flow into the inlet passage or conduit 50 in the direction of arrow 56 for filtration.

If it is desired that the filter functions should be taken out of the extracorporeal circuit, it can be bypassed through the bypass inlet portion or conduit 70. This causes flow outwardly through the outlet portion or bypass conduit 68 in the direction of arrow 64. This allows the filter to be bypassed so that it need not be used in the eventuality of clogging of the filter, or other reasons for bypassing the filter are desired.

In order to effect the bypass by the Y member 76, it is only necessary to clamp off the branch or conduit 80 by means of a clamp 90. In the alternative, in order to allow flow through the branch or conduit 80 and avoid the bypass connected to the branch of the branch or conduit 82, it is merely necessary to clamp off the bypass portion of the Y at clamp 92. This allows flow in either the filter mode through branch or conduit 80 of the Y or through the bypass mode through branch or conduit 82 of the Y.

Thus, the filter 10 can be taken out of the system by merely clamping the branch or conduit 80 by means of clamp 90 while maintaining the clamp 92 in an open position to allow for flow in the direction of arrow 96.

The bypass can also be utilized for priming the filter prior to use. This feature can save as much as 15 cc of fluid over the volume required for priming without the integrated bypass.

The filter 10 has an in depth filter element 26 comprising a cylindrical pleated filter member 98 having a filter cap 38 and supported on a bobbin support 126 to provide the filter element 26. In this manner, flow in the direction of arrow 60 can pass through the filter pleats 98 into the interior 100 of the filter element 26 as will be detailed hereinafter.

Structural Configuration

Looking more particularly at FIG. 2, which is a cross-section along lines 2—2 of FIG. 1, it can be seen that the filter 10 is comprised of the lid or top 14 overlying the dome or filter cap 38 having a domed or rounded surface 40. The rounded cone or peak 42 is shown with a rounded end 44. Furthermore, it can be seen that the groove 46 is a circular depression below the general surface of the dome or rounded surface 40. The groove 46 can be of any suitable configuration and in fact can be a flat circular rim or depression around the interface between the rounded cone or peak 42 and the dome or rounded surface 40.

The rounded cylindrical side walls 12 of the filter 10 extend upwardly and bell out slightly to provide a circular channel or groove 120. The circular groove 120 receives a circular tongue or flange 122 formed in a circular manner on the lid or top 14.

This tongue and groove jointure arrangement wherein circular tongue 122 fits into circular groove 120 can be enhanced. This can be by an adhesive or an Ultraviolet (UV) cure or such welding as is known in the art in the form of ultra-sonic welding. Alternately, a solvent can be applied to allow the two portions of the plastic to come together.

The filter 10 including the rounded cylindrical side walls 12 and the lid or top 14 and dome or filter cap 38 as well as the bottom or base wall 16 and the outlet portion or bypass conduit 68 and 70 can all be formed of plastic. This plastic can be polycarbonate, ABS, or other types of plastics including polypropylene, polyethylene, styrene-butadiene (SB) and methylene-butadienestyrene (MBS). A clear plastic is most preferred to permit visual inspection and monitoring of the action of the filter during use.

The dome or filter cap 38 is snap fit onto an elongated tubular, bobbin type of support 126 for the filter pleated member 98. This can be seen as the cylindrical bobbin or tubular support member 126 having an opening 128. The tubular support member 126 not only serves as a support for the pleated filter member 98, but together with the filter cap 38 also provides for volume displacement. Thus, the volume displacement limits the amount of blood or priming liquid necessary to pass through the filter on an effective operational basis.

The cylindrical, bobbin or tubular filter support 126 extends upwardly and expands into a flat disc-like portion 130 with the opening 128 extending therethrough. The flat disc-like portion 130 is snap fit into the dome or filter cap 38. The dome or filter cap 38 has a ledge or groove 132 surrounding the interior portion thereof in which the flat disc like portion 130 can be snap fit thereinto.

In order to enhance bonding, an Ultraviolet (UV) cure is undertaken and can be added to by means of a bonding agent.

The dome or filter cap 38 extends downwardly over the edge of the flat disc like portion 130 to provide a cover over the filter pleated member 98. This helps to prevent the entrapment of bubbles at a higher point than is desired. Further to this extent, the dome or filter cap 38 with its narrowly extending skirt shown as skirt 136 has a chamfered edge 138.

The chamfered edge 138 avoids trapping of bubbles that are entrained in the blood under a ledge of the dome or filter cap 38. This of course enhances the overall effectiveness of the disassociation of the air in the blood.

The cylindrical pleated filter member 98 is emplaced within the area or channel 140 defined by the chamfered edge or skirt 138 of filter cap 38, the underside of the flat disc like portion 130 and cylindrical base 134 of bobbin or tubular support member 126 and sealed.

The sealing can take place within the walled circular channel 140 which can be filled with a hot melt glue. This secures one end of the circular pleated filter member 98 within the cap 38 to prevent any bypass and leaking.

In this manner, fluid passing through the filter 10 does not extend within the filter cap 38 but flows into a space or circular chamber 144 surrounding the cylindrical bobbin or tubular filter support 126. This directs the blood flow along the opening or chamber 144 downwardly in the direction of arrow 146 so that it passes outwardly into the outlet portion or bypass conduit 68.

The cylindrical pleated filter element 26 is generally of a uniform cylindrical form. However, the rounded cylindrical side walls 12 of filter 10 taper inwardly to form the space 24 between the side walls which slope downwardly and inwardly. The tapering space 24 creates a situation wherein the decreasing radius or size causes the air that has been entrained to meet more resistance. The entrained air is inclined to travel upwardly through the space 24 and eventually through the vent 30.

The bobbin or filter support 126 is set within the base wall or bottom 16 of the filter 10. The bottom wall 16 of the filter 10 comprises a round circular member having a circular groove 150 which receives a rounded tongue or flange 152 of the rounded cylindrical side wall 12 projecting downwardly thereto. The circular groove 150 is formed by an exterior circular flange or raised wall 153 and an interior circular raised portion or flange 154.

A second interior raised flange or wall of a smaller radius 156 is also provided. Within these interior circular portions, flanges or walls 154 and 156 is formed a channel 158 which circumscribes the base. The channel 158 provides a space into which the bottom of the cylindrical pleated filter element or member 98 can be placed. The cylindrical pleated filter member 98 is placed in the channel 158 and sealed by means of a hot melt plastic or other type of adhesive.

With the top and bottom of the filter member or element 98 sealed as above described, blood flowing against the filter element 98 passes through the cylindrical pleated filter member 98 into the space 126. The blood flow continues downwardly around the cylindrical base member 134 in the direction of arrow 146.

The cylindrical base 134 of the cylindrical bobbin or tubular filter support member 126 has a rounded tapered portion 162 which allows for low trauma to blood flowing thereover. The cylindrical base 134 of the tubular support member 126 is supported on four support legs 164 which allow for blood flow in the direction of arrow 146.

The support legs 164 are attached to a circular or walled member 170. The circular walled member 170 supports the legs 164 and provides for rigidity. Member 170 rests within the central opening formed by the second interior wall of smaller radius 156. This can be a friction fit or slip fit based upon a slot 178 within the circular walled member 170. In the alternative it can be heat set, UV bonded, or bonded with other suitable means such as a solvent or glue.

Operationally Related Features

A most important feature of this invention is the nature of the delivery of the blood at an upward angle toward the dome or filter cap 38 and the lid or top 14.

In FIG. 2, a line 180, which is in a plane perpendicular to the central axis 168 of filter 10, is shown drawn next to the central axis line 182 of the inlet delivery passage or conduit 50. The included angle thereof is an angle in this case of 6° from the line 180 in a plane perpendicular to the axis 168 of the filter 10. This provides an upward angle of blood flow entry into the filter 10 of 6°.

It has been found that the optimum upward angle of blood flow entry is approximately in the range of 5° to 20°. At angles less than 5°, the benefits are proportionally reduced. Thus, at a slight upward inclination such as 3° or 4°, the results are proportionately less than at 5° or 6°. At upward inclination angles greater than about 20° other factors such as increased turbulence can result.

However, any slight upward inclination of the angle of introduction along the axis line 182 of conduit 50 that causes the velocity component to move upwardly against the interior of the top or lid 14 is advantageous for releasing the entrained air. This is because of the fact that the natural tendency of the air is to escape through its natural buoyancy from the blood upwardly through the outlet or vent 30. This action is enhanced by providing an upward velocity component.

This upward velocity component imparted to the blood delivery causes the blood to swirl upwardly toward the interior lid or top 14. This swirl, creating a vortex is enhanced by the rounded filter cap 38 in conjunction with the rounded peak 42.

As shown in FIG. 2, this can be seen as the blood flow of arrow 186 inwardly through the inlet passage or conduit 50 and is such where it flows spirally upwardly in the direction of arrow 188. The velocity component takes the blood upwardly against the interior walls of the lid or top 14, across cap 38 and around the peak 42 to form a vortex. This velocity component and the forming vortex drives the natural state of entrapped air upwardly and outwardly through the outlet or vent 30.

Figure 3:
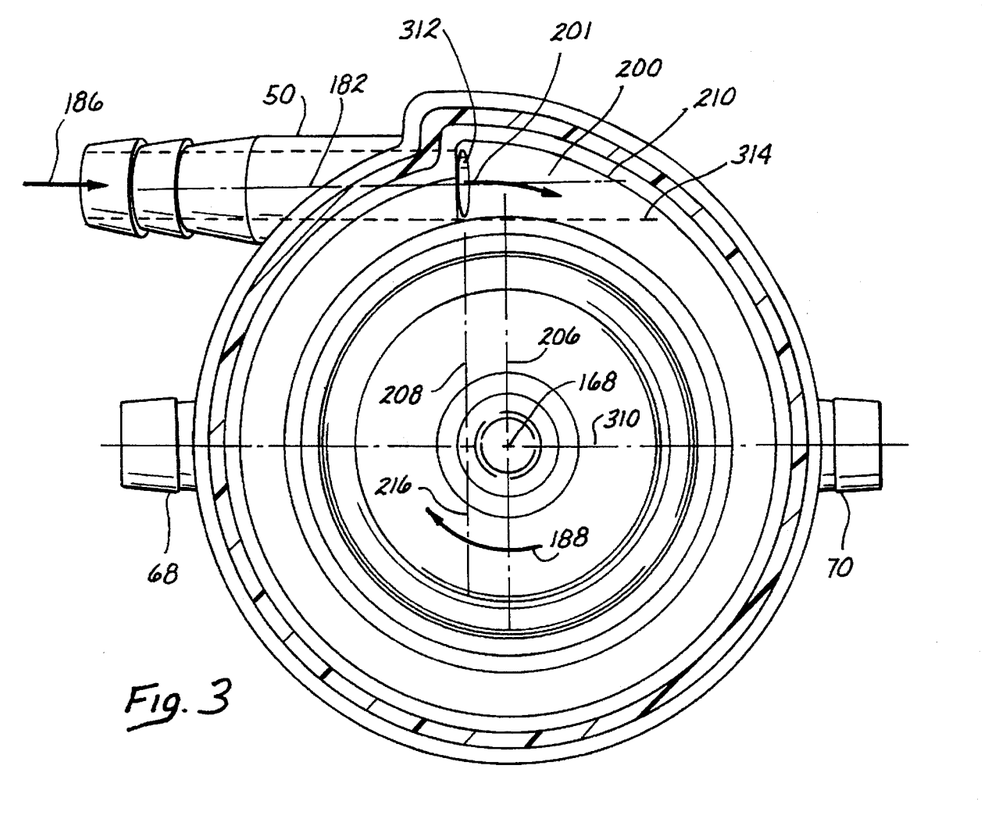
FIG. 3 shows a cross-sectional view looking through the top cover and filter cap area of this invention as seen along lines 3—3 of FIG. 2.
Figure 8:
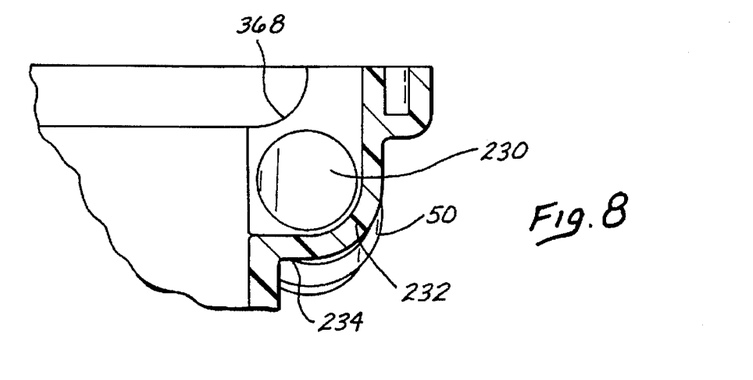
FIG. 8 shows a sectional view illustrating the curved continuous path leading from the introductory passage of the blood filter as sectioned along lines 8—8 of FIG. 7.

In order to understand the blood flow, FIG. 3 should be looked at in light of the other Figures. In particular, the direction of blood flow as to arrow 186 can be seen passing through the inlet or passage conduit 50. Flow continues into the interior tubular passage 210 which extends in an upward circular path along the peripheral interior of the walls 12. The tubular passage 210 extends in an upwardly curved path formed by curved side walls 232 for approximately three quarters of the circumference of the walls 12. Then the tubular passage continues horizontally around the top periphery of the walls 12 to end at a point 368 above the inlet 230 of conduit 50 as shown in FIG. 8. Blood flow continues spirally upwardly into the top or lid 14 of the filter 10.

For purposes of orientation, the central axis of the filter 10 is shown as axis 168 in the center. A line 310 lies in a plane which is perpendicular to the axis 168. Another line or radius 206 lies in a plane which is perpendicular to the axis 168 and to line 310.

At the point of introduction 312 between the conduit 50 and the chamber walls 12 a line 208 can be drawn. Line 208 lies in a plane which is intersected at an angle of 6° by the conduit axis 182. Moreover, axis 182 of conduit 50 does not form a tangent to and is not parallel to a tangent 314 of radius or line 206.

Due to the upward angle at which conduit axis 182 intersects the plane containing line 208 and the fact that conduit axis 182 does not form a tangent to line 206 at the point of delivery 312, the flow in the passage or tubular channel 210 begins at line 208. Here it can be seen that the initial flow begins its turn before it reaches the tangent 314 of the radius 206. This sets the initial flow back from the curved wall or channel 210. This consequently provides smoother inlet flow of the blood to prevent less blood trauma and hemolysis.

In effect, by the time the blood flow reaches the radius 206 the blood is already beginning to flow with an upward curved angular component against the curved walls of curved passage 210 to create the smooth transitional flow necessary for low hemolysis of this invention.

Starting from opening 230 of conduit 50, the curved channel or passage 210 has a gradually decreasing radius for about 85° and then the passage 210 has a constant radius. At the same time, the curved passage 210 gently rises in a curved path of about 270°. Thereafter, the curved path is planar or flat until it terminates at a point 368 which overlies opening 230 of conduit 50.

As the blood swirls upwardly against the curved passage or rounded channel 210 through the decreasing or narrowing area it achieves a greater velocity component added to its normal velocity component. The velocity components push the blood to the left side as can be seen in FIG. 6 looking downwardly through the top cover 14. In other words, the blood velocity components form a vortex having a center which is shifted to the left of radial line 206 to a point approximately lying under line 216. Since the vortex has been pushed by the velocity components of the introductory blood in the direction of line 216, the outlet or vent 30 has been oriented to a point above the displaced vortex.

The flow of the swirl pattern as indicated by arrow 188 is such where the blood flow component pushes the vortex off center. The release of entrained air from the vortex through outlet or vent 30 is enhanced by having the vent offset from the radial line 206 passing through the central axis 168 of the filter chamber defined by the rounded cylindrical side walls 12 of the filter 10.

Figure 7:
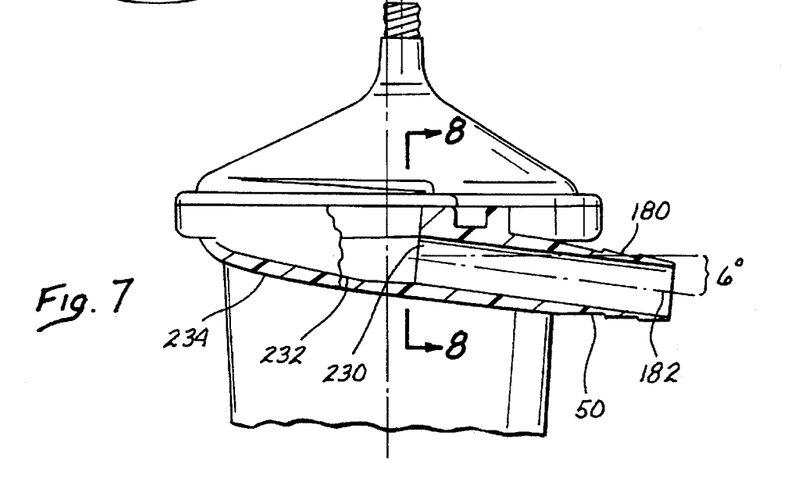
FIG. 7 shows a partially fragmented sectional view of the filter illustrating the inclined delivery passage for blood into the filter leading into a curved continuous path.

The aspects of this invention can be seen more readily as to the smooth and upward velocity movement of the blood through the introductory inlet passage or conduit 50 by viewing FIGS. 7 and 8.

FIG. 7 shows a fragmented view with the inlet passage or conduit 50 having its axial line 182 defining an upward angle of 6° from a plane which is perpendicular to the axis 168 of the filter 10 as set forth herein before. The introductory point of the blood at an opening 230 of the inlet passage or conduit 50 allows for the continuous flow against a rounded smooth interior surface or side wall 232 forming a curved passage of channel 210. This can be seen also in FIG. 8.

This rounded smooth interior surface or side wall 232 wraps around the upper portion of chamber walls 12 of the filter chamber to form the interior curved passage or channel 210. This provides for a smooth flow and directional component of blood so that sharp edges are not encountered by the blood that would create damaged cells and hemolysis.

The rounded configuration of the interior surface or side wall 232 of passage 210 rises gently around the circumference of the interior walls 12 of the filter 10. The passage 210 rises over a path of rotation of about 270° after which it follows a continuing curved path on a planar level. The ascending outer configuration is defined by the external wall 234.

With respect to the size of the passage 210, the larger initial area of the passage or channel 210 decreases gradually over a path of rotation of about 85° at which point the area or size of the channel 210 is constant.

Operation

Referring now to FIG. 2, when the inlet passage 50 is connected to an extracorporeal blood circuit, the blood flows upwardly in the direction of arrow 186. As it flows in this upward velocity component, it flows within passage or channel 210 along curved walls 232 and against the interior of the top or lid 14 as well as across the surface of filter cap 38. This upward velocity component causes the blood to flow in an upward spiral in the direction of arrow 188 one or more times around the top 14 to form a vortex.

The blood then begins to descend downwardly across the face of the dome or rounded surface 40 of the rounded dome or filter cap 38. In traveling this route, the blood has its vortex offset in the direction of the left side of FIG. 6 and to the right side of FIG. 2 so that the vortex moves toward the center of the offset outlet or vent 30. As the vortex approaches the center of the outlet or vent 30, it tends to release the entrained air more effectively for escape through the outlet or vent 30.

As the blood descends over the filter cap 38 or rounded surface 40 it follows a radial path indicated by arrow 470 through the space 24 between the rounded cylindrical side walls 12 and the cylindrical filter pleats 98 of the filter element 26. The blood tends to disassociate more bubbles while following this spiral path. This is partially due to the interior surface of the rounded cylindrical side walls 12 sloping toward the base wall 16. The decreasing size of space 24 causes the bubbles to be released more effectively.

Figure 4:
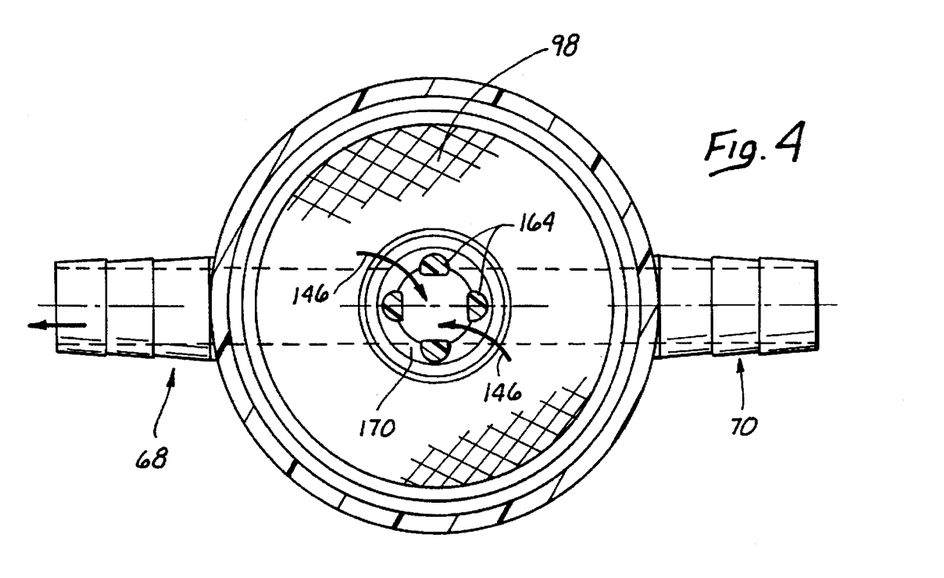
FIG. 4 shows a sectional view of the filter through the filter media and outlet area as seen in the direction of lines 4—4 of FIG. 2.

The blood then flows radially in the direction of arrow 146 through the cylindrical filter pleats 98 into the opening or chamber 164. As can be seen in FIG. 4, the blood then flows downwardly and out through the opening connected to the outlet portion or bypass conduit 68.

The features to eliminate the entrapment of bubbles, the upward velocity component of the blood at introduction, the smooth introduction along inlet passage or conduit 50 through and into the interior surface or side wall 232 as well as the overall displacement of the vortex causes substantial release of entrapped or entrained bubbles before reaching the circular pleated filter 26. This enhances the operation and improves efficiency so that the filter is deemed to be a distinct improvement over the prior art. As a consequence, this invention should be read broadly in light of the following claims which follow hereinafter.

We claim:

1. A blood filter for use in filtering blood circulating under pressure at least partially outside of a body comprising:

a blood filter defined by side walls with a top and a bottom joined to said side walls defining a vertical axis thereof;

an air outlet in said top;

a filter element surrounding at least a portion of said vertical axis;

a delivery inlet conduit for delivering blood to the interior of said filter oriented at an angle extending upwardly away from a plane which is perpendicular to the vertical axis of said filter;

an outlet conduit connected to the interior of said filter element for allowing blood to flow from said filter element to an exit conduit forming an outlet;

said air outlet is placed off center from the vertical axis of said filter at a location removed from said delivery conduit;

a filter cap overlying said filter element and sealed thereto to allow the flow of blood through said filter element toward the vertical axis of said filter element and having a rounded dome shape terminating in a rounded peak over which the blood introduced to said filter flows with a skirt overlying said filter element having a chamfer on the edge thereof for the release of air bubbles entrapped thereby; and, wherein the delivery of blood to said filter by said delivery inlet conduit causes said blood to flow upwardly against said filter cap in a circular manner creating a vortex.

2. The filter as claimed in claim 1 further comprising:

side walls which extend inwardly as they approach the bottom of said filter.

3. The filter as claimed in claim 1 further comprising:

an outlet conduit connected to a second conduit which can deliver blood directly to the outlet conduit without passing through the filter.

4. The filter as claimed in claim 1 further comprising:

an interior wall of said filter connected to said delivery inlet conduit having at least a portion thereof of a rounded cross-section conforming to the cross-section of said delivery inlet conduit to provide continuity of flow in the same rounded configuration.

5. A filter for filtering blood under pressure in a circuit flowing partially outside of a human body comprising:

a filter container formed by side walls, a bottom wall connected to said side walls, said bottom wall having an outlet conduit, and a top lid defining an axis, wherein said top lid has a centrally offset air vent allowing the release of air therefrom;

wherein said centrally offset air vent is in generally overlying relationship to an area wherein a vortex is established by blood flowing into said filter for release of air directly toward said air vent;

a filter element disposed between said side walls having a filter cap thereover;

said filter cap having a rounded dome with a rounded peak extending above said rounded dome and wherein said filter cap and peak are within at least a portion of the axis of said filter, said filter cap further having a skirt extending over said filter with a chamfered edge; and a delivery conduit connected to the interior of said filter for delivery of blood to said filter having an axis at an angle extending upwardly away from a plane which is perpendicular to the axis of said filter so that the flow of blood is delivered upwardly toward the lid of said filter and over said filter cap.

6. The filter as claimed in claim 5 wherein:

the axis of said delivery conduit and the plane perpendicularly intersecting the vertical axis of said filter has an included angle in the range of 3° to 20°.

7. The filter as claimed in claim 5 wherein:

said centrally offset air vent is displaced from said delivery conduit.

8. The filter as claimed in claim 5 further comprising:

a filter element having a substantially uniform cylindrical configuration; and, side walls of said filter container extending inwardly toward said filter element as they approach the bottom of said filter.

9. The filter as claimed in claim 5 wherein:

said outlet conduit from said filter is connected to a second conduit that can be used to bypass said filter.

10. The combination of a filter element through which blood is filtered and a chamber forming a filter wherein said chamber comprises:

a bottom with an opening underlying said filter element;

side walls extending from said bottom;

a lid connected to said side walls;

a conduit for delivery of blood to said filter disposed at an upward angle to a line in a plane intersecting the axis of said filter for delivery of blood with an upward velocity toward the lid of said filter;

a vent within said lid which is offset from the axis of said filter for releasing air from said chamber; and, a rounded wall section on said side walls connected to said delivery conduit having at least a partial cross-sectional portion thereof conforming to the interior of said delivery conduit and defining a continuous curved upward spiral path over a path of rotation of at least about 270° and having a decreasing cross-sectional area over a path of rotation of at least 85°.

11. The combination as claimed in claim 10 further comprising:

a domed cap overlying said filter element having a peak thereon wherein said domed cap has an axis generally in line with the axis of said filter.

12. The combination as claimed in claim 11 further comprising:

a bobbin on which said filter element is placed for receiving said filter element for supporting it, said bobbin having openings therethrough for the passage of blood from said filter element to said opening underlying said filter element.

13. The combination as claimed in claim 10 further comprising:

side walls that extend inwardly toward the bottom of said filter.

14. The combination as claimed in claim 10 further comprising:

a second conduit connected to said opening underlying said filter for bypassing said filter.

* * * * *